(12) United States Patent
Mori et al.

(10) Patent No.: US 11,547,308 B2
(45) Date of Patent: Jan. 10, 2023

(54) BLOOD PRESSURE MONITOR

(71) Applicant: OMRON HEALTHCARE CO., LTD., Muko (JP)

(72) Inventors: Naoki Mori, Kyoto (JP); Hiroto Sugano, Kyoto (JP); Kazuhiro Matsui, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 1070 days.

(21) Appl. No.: 16/212,532

(22) Filed: Dec. 6, 2018

(65) Prior Publication Data

US 2019/0104950 A1 Apr. 11, 2019

Related U.S. Application Data

(63) Continuation of application No. PCT/JP2017/019565, filed on May 25, 2017.

(30) Foreign Application Priority Data

Jun. 23, 2016 (JP) .............................. JP2016-124766

(51) Int. Cl.
  *A61B 5/0235* (2006.01)
  *A61B 5/022* (2006.01)
  (Continued)

(52) U.S. Cl.
  CPC .......... *A61B 5/0235* (2013.01); *A61B 5/022* (2013.01); *A61B 5/02141* (2013.01);
  (Continued)

(58) Field of Classification Search
  CPC ... A61B 5/0235; A61B 5/02141; A61B 5/022; A61B 5/02225; A61B 5/02116; A61B 5/6824
  See application file for complete search history.

(56) References Cited

U.S. PATENT DOCUMENTS 4,669,485 A * 6/1987 Russell .................. A61B 5/022
                                                        600/492
4,718,426 A * 1/1988 Russell ................ A61B 5/0235
                                                        600/490

(Continued)

FOREIGN PATENT DOCUMENTS

| JP | H7-178065 A | 7/1995 |
| JP | 2011-200290 A | 10/2011 |
| WO | WO-0057776 A1 * | 10/2000 ......... A61B 5/02007 |

*Primary Examiner* — Navin Natnithithadha
(74) *Attorney, Agent, or Firm* — Oliff PLC

(57) ABSTRACT

A blood pressure monitor of the present invention includes a cuff to be wrapped around a measurement site. The blood pressure monitor includes a unit including, as elements for blood pressure measurement, a pump, a valve, a pressure sensor, and an inner pipe connecting the pump, valve, and pressure sensor such that fluid can pass therethrough. The blood pressure monitor includes a connecting pipe connecting the cuff and the inner pipe in the unit such that fluid can pass therethrough. The blood pressure monitor includes a self failure diagnosis unit configured to determine whether or not there is a failure in a fluid system including the pump, the valve, the pressure sensor, the inner pipe, the connecting pipe, and the cuff, in a state in which the cuff is empty-wrapped into a cylindrical shape and the capacity of the cuff is restricted.

7 Claims, 17 Drawing Sheets

(51) Int. Cl.
*A61B 5/021* (2006.01)
*A61B 5/00* (2006.01)
(52) U.S. Cl.
CPC ....... *A61B 5/02225* (2013.01); *A61B 5/02116* (2013.01); *A61B 5/6824* (2013.01)

(56) References Cited

U.S. PATENT DOCUMENTS

| | | | | |
|---|---|---|---|---|
| 4,718,427 A | * | 1/1988 | Russell | A61B 5/022 |
| | | | | 600/490 |
| 4,718,428 A | * | 1/1988 | Russell | A61B 5/0235 |
| | | | | 600/490 |
| 4,953,557 A | * | 9/1990 | Frankenreiter | A61B 5/02156 |
| | | | | 600/494 |
| 2003/0065270 A1 | * | 4/2003 | Raines | A61B 5/0295 |
| | | | | 600/504 |
| 2012/0203119 A1 | * | 8/2012 | Yamashita | A61B 5/6824 |
| | | | | 600/490 |
| 2013/0006154 A1 | * | 1/2013 | Lowe | A61H 9/0092 |
| | | | | 607/104 |

* cited by examiner

FIG. 15

MAINTENANCE MENU > MEASUREMENT CAPABILITY DIAGNOSIS

| | RIGHT PRESSURE | | LEFT PRESSURE | |
|---|---|---|---|---|
| UPPER ARM | 0 mmHg | UPPER ARM | 0 mmHg |
| ANKLE | 0 mmHg | ANKLE | 0 mmHg |

PLEASE EMPTY-WRAP ALL CUFFS TO THE CALIBRATION MARK POSITION WITH THE SMALLEST CIRCUMFERENTIAL LENGTH AND THEN PRESS THE MEASURE BUTTON.

( RETURN )

MAINTENANCE MENU > MEASUREMENT CAPABILITY DIAGNOSIS  40

| | RIGHT UPPER ARM | LEFT UPPER ARM | RIGHT ANKLE | LEFT ANKLE |
|---|---|---|---|---|
| AIR LEAKAGE AMOUNT | × | × | ○ | ○ |
| PRESSURE INCREASE RATE | ○ | ○ | ○ | ○ |
| AIR DISCHARGE RATE | ○ | ○ | ○ | ○ |
| MEASUREMENT INSTANCE COUNT | ○ | ○ | ○ | ○ |

PRINT

RETURN

FIG. 17

MEASUREMENT CAPABILITY
DIAGNOSIS — 71      2016/02/23 17:25

■ DIAGNOSIS RESULTS

|  | RIGHT UPPER ARM | LEFT UPPER ARM | RIGHT ANKLE | LEFT ANKLE |
| --- | --- | --- | --- | --- |
| AIR LEAKAGE AMOUNT | ○ 4.1 mmHg/60s | ○ 3.5 mmHg/60s | ○ 4.0 mmHg/60s | ○ 3.1 mmHg/60s |
| PRESSURE INCREASE RATE | ○ 9.4 mmHg/s | ○ 10.6 mmHg/s | ○ 11.4 mmHg/s | ○ 14.1 mmHg/s |
| AIR DISCHARGE RATE | ✕ 11.4 mmHg/s | ○ 4.7 mmHg/s | ○ 4.8 mmHg/s | ○ 4.8 mmHg/s |
| MEASUREMENT INSTANCE COUNT | ○ 300 | ○ 322 | ○ 253 | ○ 261 |

■ OVERALL RESULTS
<RIGHT UPPER ARM>
A DECREASE IN MEASUREMENT CAPABILITY HAS BEEN DETECTED. PLEASE RE-WRAP THE CUFF, PRESS THE MEASUREMENT BUTTON, AND CARRY OUT DIAGNOSIS AGAIN. IF THE SAME RESULT IS DISPLAYED AGAIN, PLEASE RECEIVE MAINTENANCE SERVICE.
<LEFT UPPER ARM>
THERE IS NO PROBLEM WITH THE MEASUREMENT CAPABILITY.
<RIGHT ANKLE>
THERE IS NO PROBLEM WITH THE MEASUREMENT CAPABILITY.
<LEFT ANKLE>
THERE IS NO PROBLEM WITH THE MEASUREMENT CAPABILITY.

BLOOD PRESSURE MONITOR

This is a Continuation of International Application No. PCT/JP2017/019565 filed May 25, 2017, which claims the benefit of Japanese Application No. 2016-124766 filed Jun. 23, 2016. The disclosure of the prior applications is hereby incorporated by reference herein in its entirety.

TECHNICAL FIELD

The present invention relates to a blood pressure monitor, and more specifically relates to a blood pressure monitor that can determine whether or not there is a failure in a fluid system.

BACKGROUND ART

Conventionally, for example, Patent Document 1 (JP H7-178065A) has disclosed a blood pressure monitor that includes a blood pressure monitor main body and a compression belt (cuff) connected to the blood pressure monitor body via a tube. In a state in which an air tank with a certain capacity is attached instead of the compression belt (cuff), the blood pressure monitor performs pressure increase and pressure reduction and detects an abnormality, such as failure of an air discharge valve or air leakage.

Also, Patent Document 2 (JP 2011-200290A) has disclosed a blood pressure monitor including a blood pressure monitor body and a cuff to be connected to the blood pressure monitor body via a tube. In a state in which the cuff is wrapped around an upper arm or the like, the blood pressure monitor performs pressure increase and pressure reduction for blood pressure measurement, compares the total applied pressure that has been accumulated and stored, and a threshold value for the applied pressure corresponding to a durability limit set in advance, and if the total applied pressure exceeds the threshold, the blood pressure monitor determines that the usage has reached the durability limit.

CITATION LIST

Patent Documents

Patent Document 1: JP H7-178065A
Patent Document 2: JP 2011-200290A

SUMMARY OF INVENTION

Technical Problem

However, with the blood pressure monitor disclosed in Patent Document 1, in order to detect an abnormality, a special tool such as an air tank needs to be used, which is problematic in that its operation is troublesome for the user. Also, the user needs to store the air tank (tool), and thus there is a risk of losing the air tank.

Also, with the blood pressure monitor disclosed in Patent Document 2, determination is performed in the process of increasing and reducing the pressure of the cuff for blood pressure measurement. For this reason, although it is possible to determine the usage amount (number of instances of measurement), the blood pressure monitor is influenced by the wrapping state of the cuff on the upper arm or the like (whether the cuff is wrapped tightly or loosely), and therefore it is difficult to determine a failure such as a pressure increase rate abnormality or a gas discharge rate abnormality.

In view of this, the present invention aims to provide a blood pressure monitor according to which it is possible to determine whether or not there is a failure in a fluid system due to a user only performing a simple operation without using a special tool.

Solution to the Problem

In order to solve the foregoing problem, a blood pressure monitor of the present invention is a blood pressure monitor for performing blood pressure measurement, including:

a cuff to be wrapped around a measurement site;

a unit including, as elements for blood pressure measurement, a pump, a valve, a pressure sensor, and an inner pipe connecting the pump, valve, and pressure sensor such that fluid can pass therethrough; and a connecting pipe connecting the cuff and the inner pipe in the unit such that fluid can pass therethrough, wherein the cuff is provided with marks serving as references for setting a dimension around a cylinder of the cuff when empty-wrapping, in which only the cuff is wrapped into a cylindrical shape with nothing in the center of the cuff, is performed, and the blood pressure monitor comprises a self failure diagnosis unit configured to determine whether or not there is a failure in a fluid system including the pump, the valve, the pressure sensor, the inner pipe, the connecting pipe, and the cuff, in a state in which the cuff is empty-wrapped into a cylindrical shape in alignment with the marks and the capacity of the cuff is restricted.

In the present specification, the cuff being "empty-wrapped" into a cylindrical shape means that the cuff is not wrapped around a measurement site, and only the cuff is wrapped into a cylindrical shape with nothing in the center.

With the blood pressure monitor of the present invention, a fluid is sent into the cuff from the pump mounted inside of the unit, through the inner pipes and the connecting pipe, or a fluid is discharged from the cuff through the connecting pipe, the inner pipes, and the valve. Accordingly, the pressure in the cuff is increased or reduced. Also, fluctuation of the arterial volume that occurs in an artery at the measurement site is detected by the pressure sensor (mounted in the unit) via the pressure of the cuff (cuff pressure), through the connecting pipe and the inner pipes. A blood pressure value is obtained using a known oscillometric method, for example, based on the detected pressure. Furthermore, with this blood pressure monitor, the cuff is provided with marks serving as references for setting a dimension around a cylinder of the cuff when empty-wrapping, in which only the cuff is wrapped into a cylindrical shape with nothing in the center of the cuff, is performed. Also, in a state in which the cuff is empty-wrapped into a cylindrical shape in alignment with the marks and the capacity of the cuff is restricted, the self failure diagnosis unit determines whether or not there is a failure in the fluid system including the pump, the valve, the pressure sensor, the inner pipes, the connecting pipe, and the cuff. Accordingly, it is possible to determine whether or not there is a failure in the fluid system due to the user (indicates a medical professional such as a doctor or nurse; may be a measurement subject or a maintenance serviceman) only performing a simple operation (mainly an operation of empty-wrapping the cuff) without using a special tool. Moreover, since the circumferential length of the cuff (the dimension around the cylinder) is constant due to being empty-wrapped in alignment with the marks, the capacity of the cuff is restricted with good reproducibility. As a result, the accuracy with which the self failure diagnosis unit determines whether or not there is a failure increases.

With a blood pressure monitor of an embodiment, lower limit values and upper limit values are set in advance for a plurality of measurement items including at least a pressure increase rate, an air leakage amount, and an air discharge rate, according to a restricted capacity of the fluid system including the restricted capacity of the cuff, and the self failure diagnosis unit determines whether or not the plurality of measurement items including at least the pressure increase rate, the air leakage amount, and the air discharge rate are acceptable by comparing the plurality of measurement items with the upper limit values or lower limit values set in advance according to the restricted capacity of the fluid system.

With the blood pressure monitor of this embodiment, the self failure diagnosis unit determines whether or not multiple measurement items including at least the pressure increase rate, the air leakage amount, and the air discharge rate are acceptable by comparing each of them with the upper limit value or lower limit value set in advance in correspondence to the restricted capacity of the fluid system. Accordingly, it is possible to suitably determine whether or not the multiple measurement items are acceptable.

With a blood pressure monitor of an embodiment, the cuff contains a fluid bladder that is in communication with the connecting pipe between an inner cloth that is to come into contact with the measurement site and an outer cloth opposing the inner cloth, and a curler that keeps the shape of the cuff in a cylindrical shape to be wrapped around the measurement site in a natural state and is a core in the empty-wrapped state is included between the outer cloth and the fluid bladder.

Also, the "inner cloth" and "outer cloth" are not only cloths, and may be composed of single-layer or multi-layer resin. Generally, in order to compress the measurement site, the inner cloth has a large elasticity, and the outer cloth is set to be substantially non-elastic (or to have a smaller elasticity compared to the inner cloth).

The "curler" is a member that has a shape that, in its natural state, is curved into an approximately cylindrical shape to be wrapped around the measurement site, and is suitably bendable for convenience in attaching and detaching the cuff to and from the measurement site.

With the blood pressure monitor of this embodiment, in the natural state, the shape of the cuff is kept in the cylindrical shape to be wrapped around the measurement site by the curler. Accordingly, the operation of attaching and detaching the cuff to and from the measurement site is easy for the user. Also, in order to determine whether or not there is a failure in the fluid system using the self failure diagnosis unit, when the user empty-wraps the cuff, the curler serves as a core (the curler is bent such that its curvature increases from the natural state, generating a repulsive force), and therefore the cuff can be strongly empty-wrapped with ease.

With a blood pressure monitor of an embodiment, the cuff is provided with calibration marks in a lengthwise direction of the cuff as the marks.

The "lengthwise direction" of the cuff indicates the direction corresponding to the circumferential direction of the measurement site when the cuff is wrapped around the measurement site.

With a blood pressure monitor of this embodiment, the cuff is provided with calibration marks in a lengthwise direction of the cuff as the marks. Accordingly, when the user empty-wraps the cuff into a cylindrical shape, if the user performs empty-wrapping in alignment with a specific position of the calibration marks, the circumferential length (dimension around the cylinder) of the cuff is constant, and the capacity of the cuff is restricted with good reproducibility to a certain amount according to the circumferential length. As a result, the accuracy with which the self failure diagnosis unit determines whether or not there is a failure increases.

A blood pressure monitor of an embodiment includes a control unit configured to, in response to operation input, set a measurement capability diagnosis mode for causing the self failure diagnosis unit to operate, separately from a mode for performing the blood pressure measurement.

With the blood pressure monitor of this embodiment, in response to operation input, the control unit sets a measurement capability diagnosis mode for causing the self failure diagnosis unit to operate, separately from a mode for performing the blood pressure measurement. Accordingly, the user can cause the self failure diagnosis unit to determine whether or not there is a failure in the fluid system by performing operation input to set the blood pressure monitor to the measurement capability diagnosis mode.

A blood pressure monitor of an embodiment includes a first output unit configured to output results of determining whether or not each of the plurality of measurement results is acceptable.

With the blood pressure monitor of this embodiment, the first output unit outputs the results of determining whether or not each of the plurality of measurement items is acceptable. Accordingly, the user can find out the results of determining whether or not each of the plurality of measurement items is acceptable.

With a blood pressure monitor of an embodiment, a plurality of the cuffs are provided, the unit includes an element for blood pressure measurement, corresponding to each cuff, the cuffs and the corresponding inner pipes in the unit are connected by the connecting pipe, and the self failure diagnosis unit determines whether or not there is a failure in each fluid system corresponding to the cuffs.

With the blood pressure monitor of this embodiment, a plurality of the cuffs are provided, the unit includes an element for blood pressure measurement, corresponding to each cuff, and the cuffs and the corresponding inner pipes in the unit are connected by the connecting pipe. Accordingly, the blood pressure monitor can be applied to blood pressure pulse wave measurement of the arms and legs, or the like, for example. Furthermore, with this blood pressure monitor, the self failure diagnosis unit determines whether or not there is a failure in each fluid system corresponding to the cuffs. Accordingly, it is possible to determine which of the multiple cuffs corresponds to the fluid system in which a failure has occurred.

Note that the units may be constituted separately from each other in correspondence with the multiple cuffs. Also, one unit may be provided for multiple cuffs, and elements for blood pressure measurement corresponding to the multiple cuffs may be mounted in that one unit.

A blood pressure monitor of an embodiment includes a second output unit configured to output results of determining whether or not there is a failure in each fluid system corresponding to the cuffs.

With the blood pressure monitor of this embodiment, the second output unit outputs the result of determining whether or not there is a failure for each fluid system corresponding to the cuffs. Accordingly, the user can find out the result of determining whether or not there is a failure for each fluid system corresponding to the cuffs.

Advantageous Effects of the Invention

As is evident from the foregoing description, with the blood pressure monitor of the present invention, it is possible to determine whether or not there is a failure in a fluid system due to a user only performing a simple operation without using a special tool.

BRIEF DESCRIPTION OF DRAWINGS

FIG. 15 is a diagram showing a message displayed on a display screen of a main unit when the measurement capability diagnosis mode starts.

FIG. 16 is a diagram illustrating a result of measurement capability diagnosis displayed on the display screen of the main unit.

FIG. 17 is a diagram illustrating a printed-out result of measurement capability diagnosis.

DESCRIPTION OF EMBODIMENTS

Figure 1:
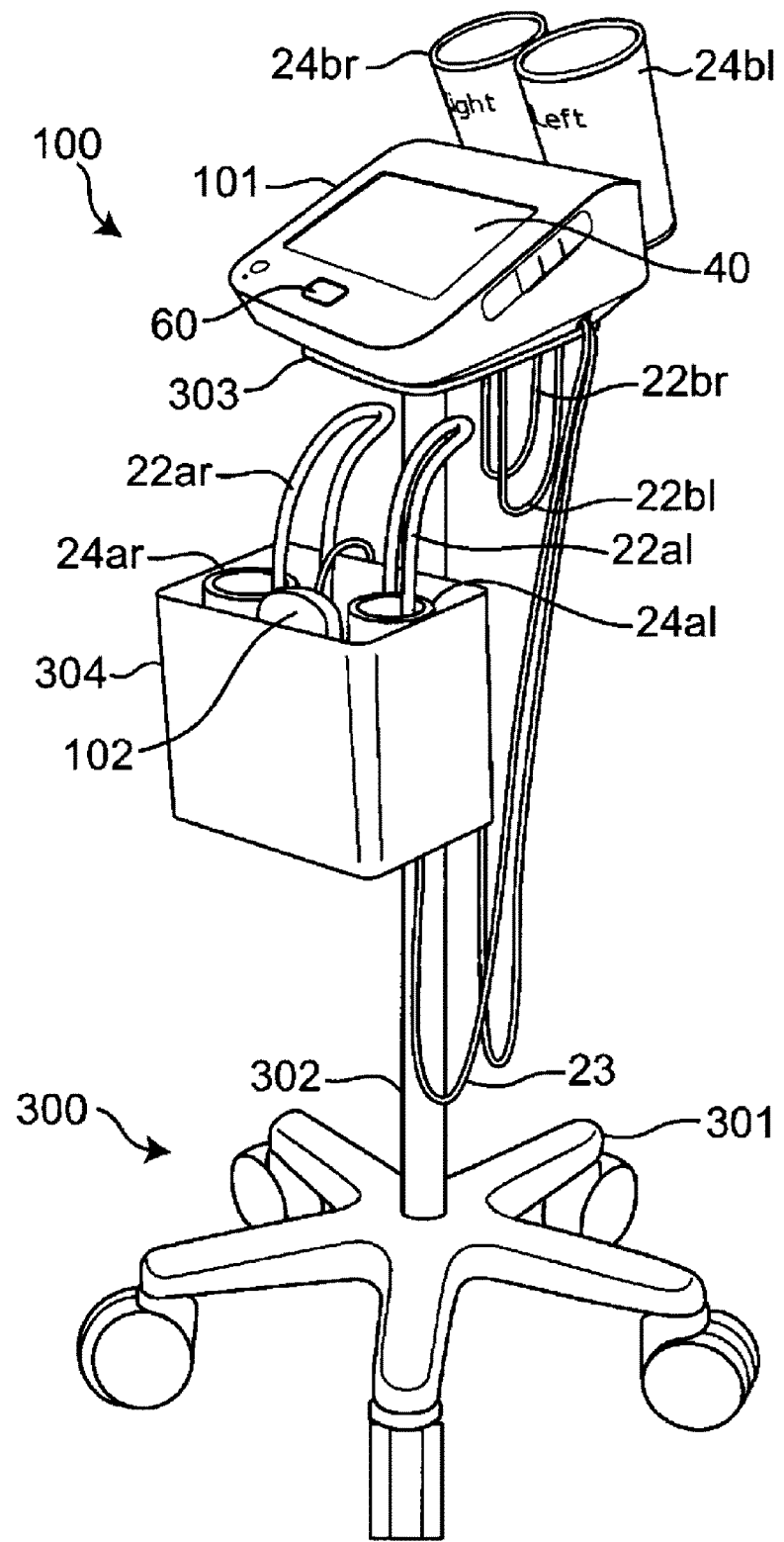
FIG. 1 is a perspective view showing a state in which a blood pressure pulse wave measurement apparatus serving as an embodiment of a blood pressure monitor of the present invention is stored in a storage wagon.

Hereinafter, embodiments of the present invention will be described in detail with reference to the drawings.
Overall Configuration of Apparatus FIG. 1 shows a state in which a blood pressure pulse wave measurement apparatus 100 serving as an embodiment of the blood pressure monitor of the present invention is stored in a storage wagon 300. The blood pressure pulse wave measurement apparatus 100 includes a main unit 101, an ankle unit 102, and four cuffs 24*ar*, 24*al*, 24*br*, and 24*br*. The storage wagon 300 includes legs 301 with casters, a support column 302 provided in a standing manner on the legs 301, a placement platform 303 attached to the leading end of the support column 302, and a storage box 304 that is attached to the support column 302 and is open upwards. The main unit 101 is placed on the placement platform 303. The storage box 304 contains the ankle unit 102 and cuffs 24*ar* and 24*al* for the right ankle (right lower limb) and the left ankle (left lower limb). The cuffs 24*br* and 24*bl* for the right upper arm (right upper limb) and the left upper arm (left upper limb) are held by being hung on hooks 101*e* and 101*f* (shown in FIG. 2) provided on the rear portion of the main unit 101.

The ankle unit 102 and the cuffs 24*ar* and 24*al* for the right ankle (right lower limb) and the left ankle (left upper limb) are connected such that a fluid can flow therethrough by connecting pipes 22*ar* and 22*al* for allowing air for increasing the cuff pressure to flow. Similarly, the main unit 101 and the cuffs 24*br* and 24*bl* for the right upper arm (right upper limb) and the left upper arm (left upper limb) are connected such that a fluid can flow therethrough by connecting pipes 22*br* and 22*bl* for allowing air for increasing the cuff pressure to flow. Also, the main unit 101 is connected by a connection cable 23 to the ankle unit 102 such that electric power can be supplied and communication is possible.

Figure 2:
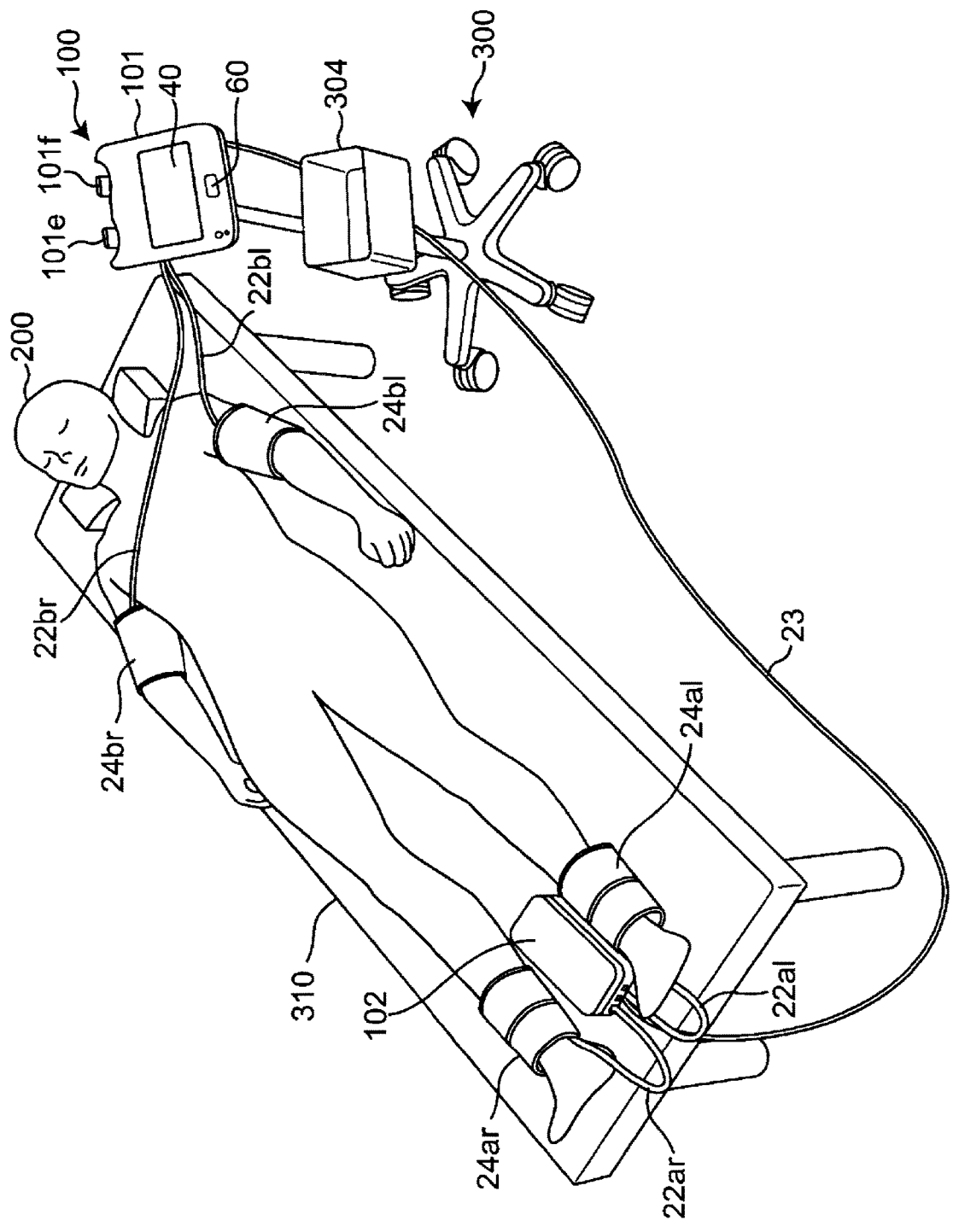
FIG. 2 is a perspective view showing a manner in which the blood pressure pulse wave measurement apparatus is used.

FIG. 2 shows a manner in which the blood pressure pulse wave measurement apparatus 100 is used. A measurement subject 200 is lying face up on the bed 310. The ankle unit 102 is taken out of the storage box 304 and is placed on the bed 310 between the right ankle and the left ankle of the measurement subject 200.

The cuffs 24*ar*, 24*al*, 24*br*, and 24*bl* are attached to the limbs of the measurement subject 200. In this example, the cuffs 24*ar*, 24*al*, 24*br*, and 24*bl* are attached so as to wrap around the right ankle (right lower limb), the left ankle (left lower limb), the right upper arm (right upper limb), and the left upper arm (left upper limb) in one direction (a spiral shape in a cross-sectional view of the limb viewed in the lengthwise direction) along the circumferential direction.

Figure 6:
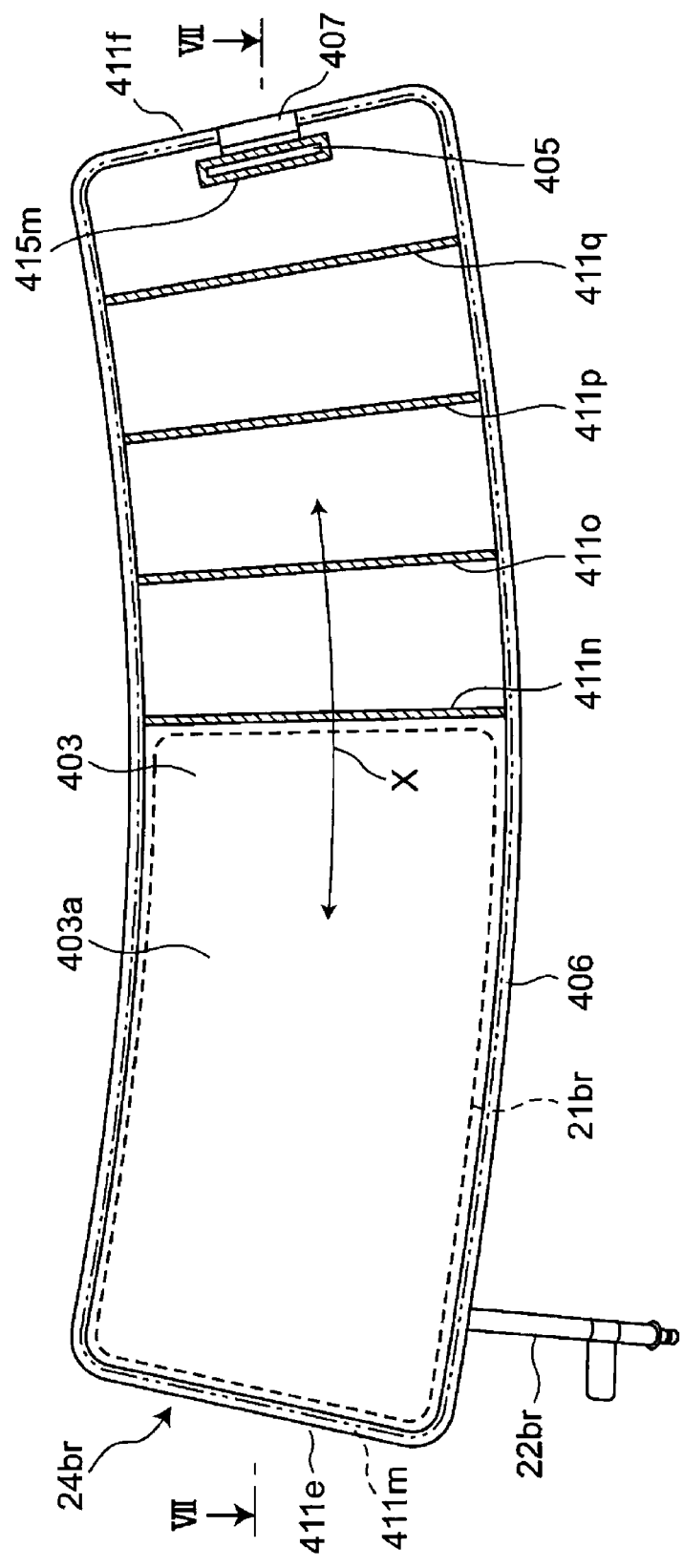
FIG. 6 is a diagram showing a cuff of the blood pressure pulse wave measurement apparatus in an unfolded state.
Figure 7:
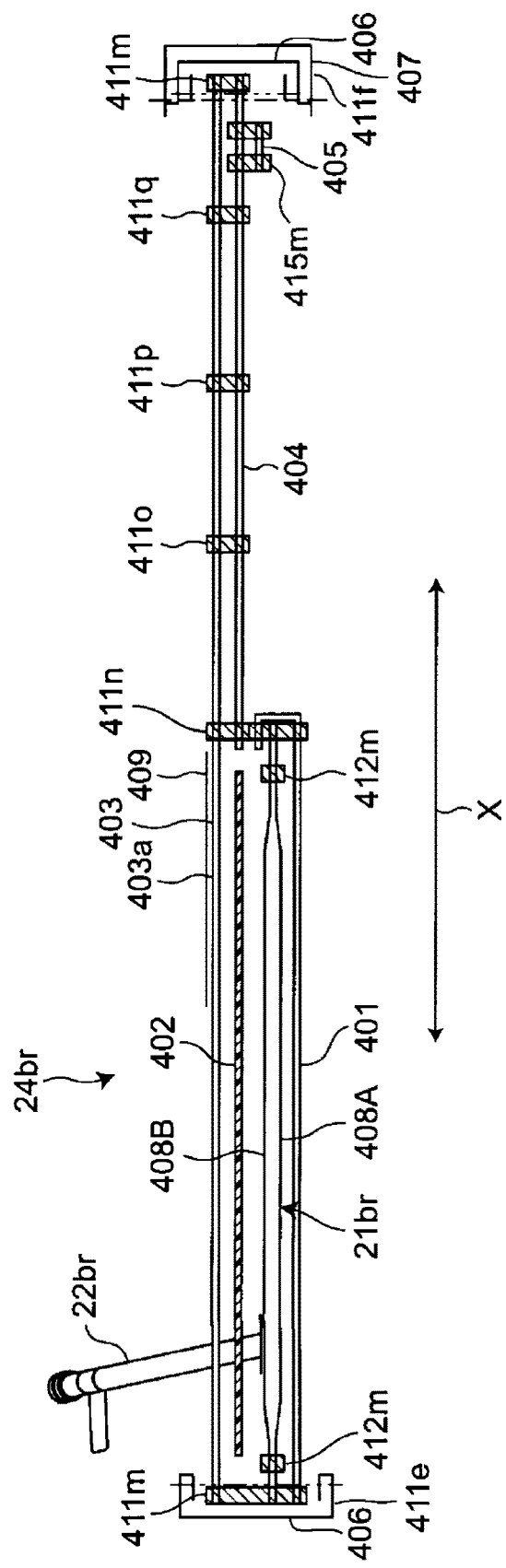
FIG. 7 is a diagram schematically showing a cross-section taken along line VII-VII in FIG. 6 and viewed in the direction of arrows.

For example, FIG. 6 shows a view of the cuff 24*br* toward an inner cloth 401 in an unfolded state. Also, FIG. 7 schematically shows a cross section taken along line VII-VII in FIG. 6. As can be understood from FIG. 7, the cuff 24*br* includes an inner cloth 401 that extends to a region located approximately halfway from one end (the end portion that is the inner circumferential end when the cuff is attached to a limb) 411*e* in the lengthwise direction X of the cuff, and an outer cloth 403 that opposes the inner cloth 401 and extends to another end (the end portion that is the outer circumferential end when the cuff is attached to a limb) 411*f* from the one end 411*e*. A fluid bladder 21*br* that extends in the lengthwise direction X along the inner cloth 401 is contained between the inner cloth 401 and the outer cloth 403. Also, a curler 402 that extends in the lengthwise direction X along the fluid bladder 21*br* is provided between the outer cloth 403 and the fluid bladder 21*br*. Furthermore, a reinforcing cloth 404 is provided in opposition on the inner side (underside) of a region of the outer cloth 403 located past the inner cloth 401 in the lengthwise direction X (region taking up the approximate right half in FIG. 7). In FIGS. 6 and 7, welding locations 411*m* on the circumferential edges of the opposing cloths and the welding locations 411*n*, 411*o*, 411*p*, and 411*q* of the interior are indicated with diagonal lines.

The inner cloth 401 shown in FIG. 7 is composed of a cloth that is woven and has a large flexibility in order to compress a limb serving as a measurement site. The outer cloth 403 and the reinforcing cloths 404 are composed of a cloth that is woven and has a very small flexibility (is substantially inflexible) compared to the inner cloth 401. Small loops (not shown) are provided on an outer surface 403*a* of the outer cloth 403 so as to engage with a later-described hook-and-loop fastener (hooks) 405.

The fluid bladder 21*br* is formed into a bladder shape by causing two sheets 408A and 408B made of a stretchable material to oppose each other and welding the circumferential edges 412*m* of the sheets 408A and 408B together (the welding locations are indicated with diagonal lines in FIG. 7). In order to supply or discharge air serving as a fluid to or from the fluid bladder 21*br*, the connecting pipe 22*br* is integrally connected to and in communication with the fluid bladder 21*br*.

The curler 402 has a shape that is bent into an approximately cylindrical shape to be wrapped around a limb in its natural state. The curler 402 is made of a plastic material that is suitably flexible for convenience in attaching and detaching the cuff to and from a limb. Accordingly, the operation of attaching and detaching the cuff 24*br* to and from a limb is easy for the user.

The hook-and-loop fastener 405 is attached through welding to a region of the reinforcing cloth 404 near the outer circumferential end 411 in the lengthwise direction X (in FIG. 7, the welding location 415*m* on the circumferential edge of the hook-and-loop fastener 405 is indicated with diagonal lines). The hook-and-loop fastener 405 has hook-shaped raisings (not shown) and can be fixed detachably to the outer surface 403*a* of the outer surface 403.

Also, calibration marks 409 in the lengthwise direction X are provided on the outer surface 403*a* of the outer cloth 403. In this example, the calibration marks 409 are marks (having a specific color) added at 5-mm intervals in the lengthwise direction X. The calibration marks 409 are guides for determining the dimension (circumferential length) around the cylinder of the cuff 24*br* when attaching the cuff 24*br* (and when performing later-described empty-wrapping).

The circumferential edge of the cuff 24*br* is covered by an edge cover 406 over the entire circumference. The edge cover 406 is attached through sewing so as to straddle the front and underside of the circumferential edge of the cuff 24*br*. Furthermore, a positioning mark 407 is attached to the outer circumferential end 411*f* through sewing so as to straddle the front and underside of the outer circumferential end 411*f*. In FIGS. 6 and 7, the sewing locations are indicated by two-dot chain lines. The color of the positioning mark 407 is set to be the same as the mark color of the calibration marks 409.

The other cuffs 24*ar*, 24*al*, and 24*bl* are configured similarly to the cuff 24*br*.

Figure 3:
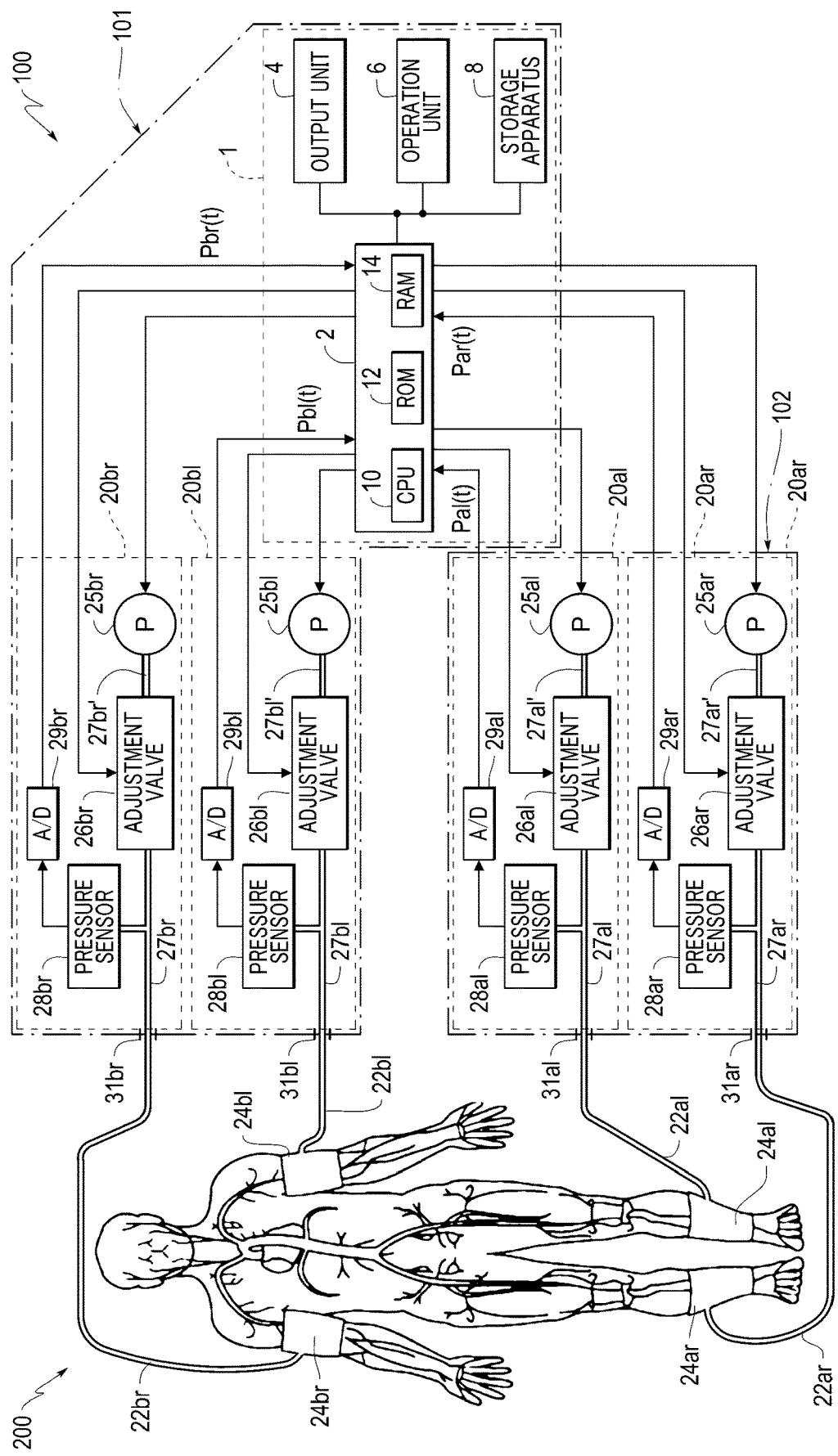
FIG. 3 is a diagram showing a block configuration of a control system of the blood pressure pulse wave measurement apparatus.

Note that in the following description, the cuffs 24*ar*, 24*al*, 24*br*, and 24*bl* will be referred to collectively as "cuffs 24" if it is not necessary to make a distinction therebetween.
Block Configuration of Control System FIG. 3 shows a block configuration of a control system of the blood pressure pulse wave measurement apparatus 100. The ankle unit 102 includes two detection units 20*ar* and 20*al*. The main unit 101 includes an information processing unit 1 and two detection units 20*br* and 20*bl*.

The detection units 20*ar*, 20*al*, 20*br*, and 20*bl* include hardware that is needed to detect pulse waves of the limbs of the measurement subject 200. The configurations of the detection units 20*ar*, 20*al*, 20*br*, and 20*bl* may all be similar, and therefore the detection units 20*ar*, 20*al*, 20*br*, and 20*bl* will be collectively referred to as "detection units 20" unless it is necessary to make a distinction therebetween.

The information processing unit 1 includes a control unit 2, an output unit 4, an operation unit 6, and a storage apparatus 8.

The control unit 2 is an apparatus that performs overall control of the blood pressure pulse wave measurement apparatus 100, and is mainly constituted by a computer including a CPU (Central Processing Unit) 10, a ROM (Read Only Memory) 12, and a RAM (Random Access Memory) 14.

The CPU 10 corresponds to an arithmetic processing unit, reads out programs stored in advance in the ROM 12, and executes the programs while using the RAM 14 as a work memory.

Also, the output unit 4, the operation unit 6, and the storage apparatus 8 are connected to the control unit 2. The output unit 4 outputs the measured pulse wave, pulse wave analysis results, and the like. The output unit 4 may be a display device constituted by an LED (Light Emitting Diode) or an LCD (Liquid Crystal Display), or the like, or may be a printer (driver). In this example, as shown in FIGS. 1 and 2, a display screen 40 of an LCD is provided as the output unit 4 on the upper surface of the main unit 101.

An operation unit 6 shown in FIG. 3 receives instructions from the user. In this example, as shown in FIGS. 1 and 2, an operation switch 60 is provided as the operation unit 6 on the upper surface of the main unit 101. The user can input instructions such as turning on and off the power, starting blood pressure measurement, setting the mode, starting measurement capability diagnosis, and the like, using the operation switch 60.

The storage apparatus 8 shown in FIG. 3 stores various types of data and programs. The CPU 10 of the control unit 2 performs reading out and writing of data and programs stored in the storage apparatus 8. The storage apparatus 8 may be constituted by a hard disk, a non-volatile memory (e.g., a flash memory), a detachable external storage medium, or the like, for example.

Next, a configuration of the detection units 20 will be described in detail.

The detection unit 20*br* detects a pulse wave of the right upper arm by adjusting and detecting the internal pressure of the cuff 24*br* (hereinafter referred to as "cuff pressure") attached to the right upper arm of the measurement subject 200. More accurately, the cuff pressure means the internal pressure of the fluid bladder 21*br*.

As elements for blood pressure measurement, the detection unit 20*br* includes: pressure sensors 28*br*; an adjustment valve 26*br*; a pressure pump 25*br*; inner pipes 27*br* and 27*br'* that connect the pressure sensors 28*br*, the adjustment valve 26*br*, and the pressure pump 25*br* such that a fluid can flow therethrough; and an A/D (Analog to Digital) conversion unit 29br. The inner pipe 27br is connected to the connecting pipe 22br via the pipe connector 31br such that the fluid can flow therethrough.

The pressure sensors 28br are detection sites for detecting pressure fluctuations transmitted from the cuff 24br via the connecting pipe 22br and the inner pipe 27br, and in an example, multiple sensor elements arranged at a predetermined interval in a semiconductor chip composed of single-crystal silicon or the like are included. The pressure fluctuation signal detected by the pressure sensor 28br is converted into a digital signal by the A/D conversion unit 29br and is input to the control unit 2 as a pulse wave signal pbr(t).

The adjustment valve 26br is inserted between the pressure pump 25br and the cuff 24br and keeps the pressure used to increase the pressure of the cuff 24br in a predetermined range during measurement. The pressure pump 25br operates according to a detection command from the control unit 2 and supplies air to the fluid bladder 21br in the cuff 24br in order to increase the pressure of the cuff 24br.

Due to this pressure, the cuff 24br is pressed to the measurement site and the pressure changes corresponding to the pulse wave of the right upper arm are transmitted to the detection unit 20br via the connecting pipe 22br. The detection unit 20br detects the pulse wave of the right upper arm by detecting the transmitted pressure changes.

As elements for blood pressure measurement, the detection unit 20bl also similarly includes: pressure sensors 28bl; an adjustment valve 26bl; a pressure pump 25bl; inner pipes 27bl and 27bl' that connect the pressure sensors 28bl, the adjustment valve 26bl, and the pressure pump 25bl such that a fluid can flow therethrough; and an A/D conversion unit 29bl. The inner pipe 27bl is connected to the connecting pipe 22bl via the pipe connector 31bl such that the fluid can flow therethrough.

Also, as elements for blood pressure measurement, the detection unit 20ar includes: pressure sensors 28ar; an adjustment valve 26ar; a pressure pump 25ar; inner pipes 27ar and 27ar' that connect the pressure sensors 28ar, the adjustment valve 26ar, and the pressure pump 25ar such that a fluid can flow therethrough; and an A/D conversion unit 29ar. The inner pipe 27ar is connected to the connecting pipe 22ar via the pipe connector 31ar such that the fluid can flow therethrough.

As elements for blood pressure measurement, the detection unit 20al also similarly includes: pressure sensors 28al; an adjustment valve 26al; a pressure pump 25al; inner pipes 27al and 27al' that connect the pressure sensors 28al, the adjustment valve 26al, and the pressure pump 25al such that a fluid can flow therethrough; and an A/D conversion unit 29al. The inner pipe 27al is connected to the connecting pipe 22al via the pipe connector 31al such that the fluid can flow therethrough.

The functions of the portions in the detection units 20bl, 20ar, and 20al are similar to those of the detection unit 20br, and therefore detailed description thereof will not be repeated. Also, if there is no need to make a distinction between the portions in the detection units 20, the reference signs "ar", "br", and the like will be omitted in the description. For example, if there is no need to make a distinction, the inner pipes will be denoted as "inner pipes 27 and 27'".

Blood Pressure Pulse Wave Measurement

Figure 4:
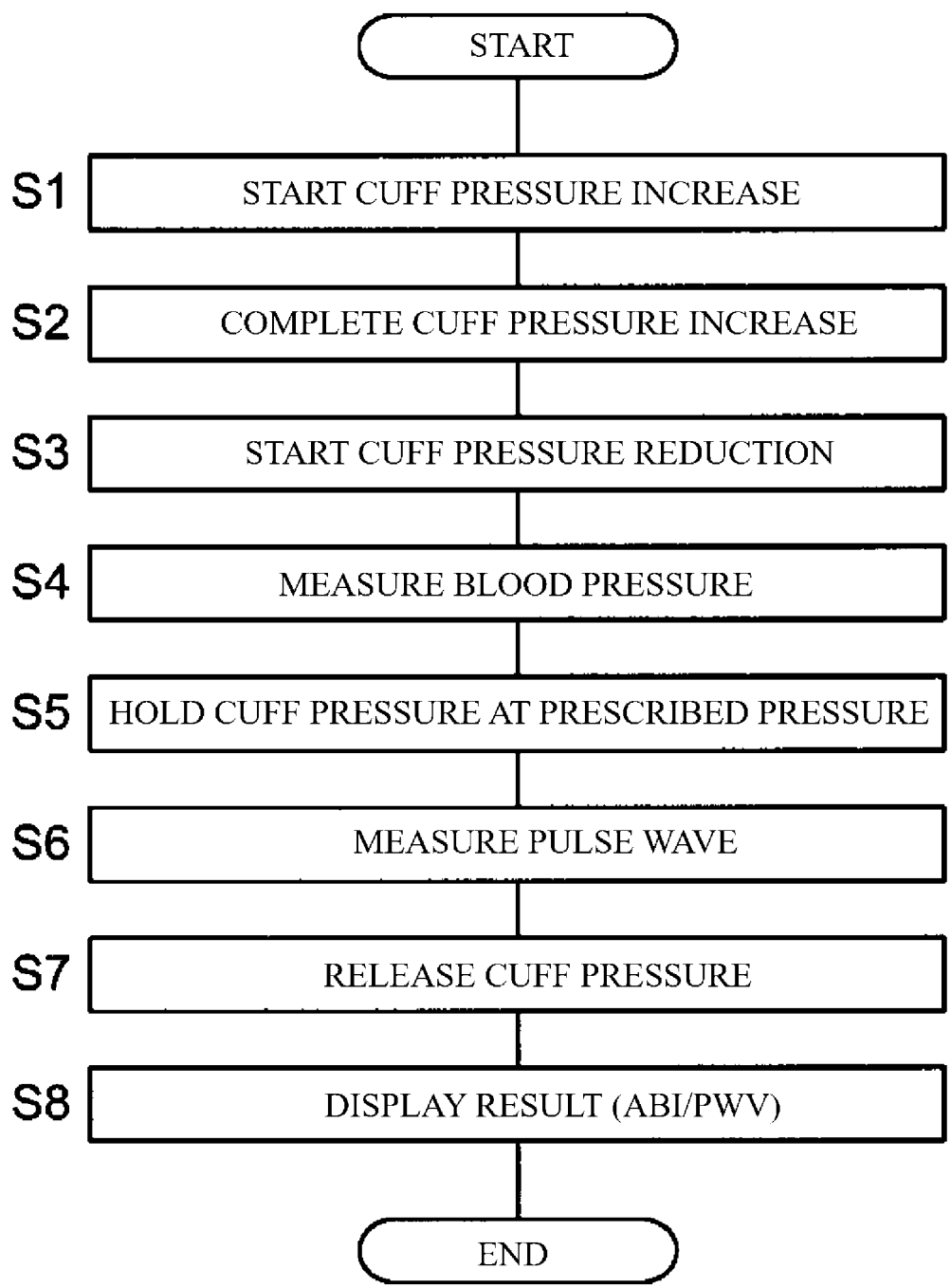
FIG. 4 is a diagram showing a flow of blood pressure pulse wave measurement processing performed by the blood pressure pulse wave measurement apparatus.

The blood pressure pulse wave measurement apparatus 100 performs blood pressure value measurement by means of a known oscillometric method as shown in the processing flow of FIG. 4 through control performed by the control unit 2 (in particular, the CPU 10). Also, the blood pressure pulse wave measurement apparatus 100 performs pulse wave detection to obtain a brachial-ankle pulse wave velocity baPWV as the pulse wave velocity, and to obtain an ankle brachial index as the upper limb-lower limb blood pressure ratio. As is known, the brachial-ankle pulse wave velocity baPWV is an index indicating the hardness of blood vessels, and the ankle brachial index ABI is an index indicating clogging of blood vessels.

Specifically, when measurement is started, as shown in step S1 of FIG. 4, the CPU 10 drives the pressure pump 25 in the detection units 20, sends air into the fluid bladder 21 in the cuff 24 through the inner pipes 27 and 27' and the connecting pipe 22, and starts increasing the pressure of the cuffs 24. Then, as shown in step S2, the cuff pressure is increased to a predetermined pressure (a pressure higher than the systolic pressure of the measurement subject 200) while the cuff pressure is observed with the pressure sensor 28, and then the pressure pump 25 is stopped (complete cuff pressure increase). Next, as shown in step S3, the adjustment valve 26 is adjusted to discharge the air from the fluid bladder 21 through the connecting pipe 22, the inner pipes 27 and 27', and the adjustment valve 26. Accordingly, the pressure reduction of the cuffs 24 is started, and the cuff pressures gradually decrease. In this pressure reduction process, fluctuations in arterial volume that occur in an artery at the measurement site pass through the connecting pipe 22 and the inner pipes 27 and 27' via the cuffs 24 (fluid bladder 21) are detected as a pulse wave signal by the pressure sensor 28. Also, as shown in step S4, based on the amplitude of this pulse wave signal, the systolic blood pressure and the diastolic blood pressure are calculated by applying a predetermined algorithm using a known oscillometric method (measure blood pressure). In addition, the CPU 10 functions as an upper limb-lower limb blood pressure ratio acquisition unit and calculates the ankle-brachial index ABI=(ankle systolic blood pressure)/(upper arm systolic blood pressure) for the left half of the body and for the right half of the body of the measurement subject 200. Also, in this example, the pulse (units: beats per minute) is also calculated. Note that the calculation of the blood pressure is not limited to the pressure reduction process and may be performed in the pressure increase process.

Figure 5:
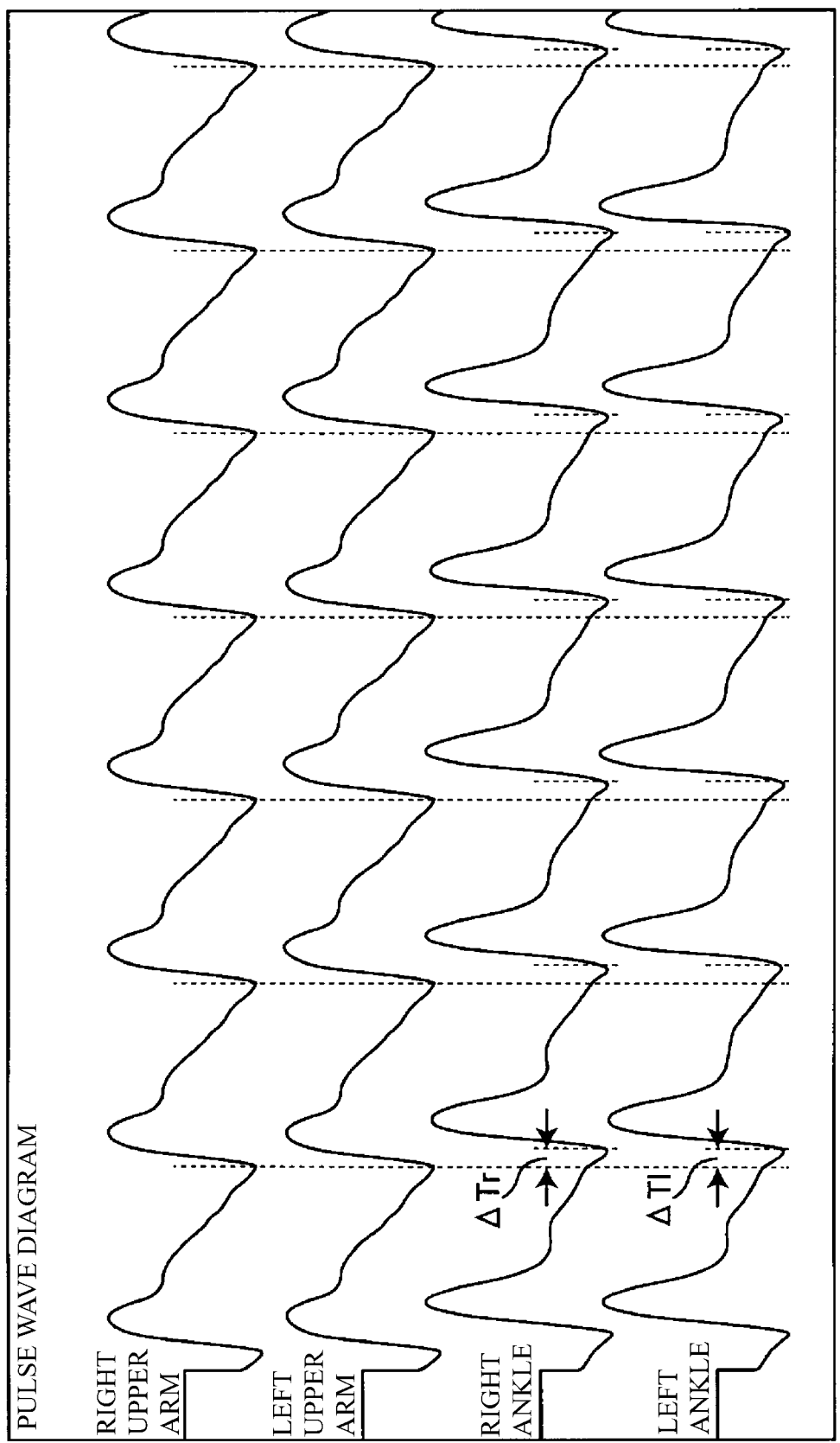
FIG. 5 is a diagram showing a pulse wave waveform detected by a pressure sensor of the blood pressure pulse wave measurement apparatus.

Next, as shown in step S5, the adjustment valve 26 is closed and the cuff pressure is held at a prescribed pressure (e.g., about 50 mmHg). In this state, as shown in step S6, the CPU 10 functions as the pulse wave velocity acquisition unit and measures the pulse wave using the pressure sensor 28. At this time, a pulse wave waveform such as that shown in FIG. 5 is obtained, for example. In this example, a delay in the rising edge of the waveform for the left ankle with respect to the rising edge of the waveform for the right upper arm of the measurement subject 200 is $\Delta Tl$. Also, the delay in the rising edge of the waveform for the right ankle with respect to the rising edge of the waveform for the right upper arm of the measurement subject 200 is $\Delta Tr$. The brachial-ankle pulse wave velocity baPWV is calculated for the right upper arm-left upper arm and the right upper arm-right ankle of the measurement subject 200 according to the following equation based on the delays $\Delta Tl$ and $\Delta Tr$.

$$baPWV=(La-Lb)/\Delta T$$

Here, La indicates the distance from the aortal root to the ankle, and Lb indicates the distance from the aortal root to the upper arm. $\Delta T$ indicates $\Delta Tl$ or $\Delta Tr$ (for the sake of simplicity, the signs "l" and "r" are omitted).

When measurement is complete, as shown in step S7 of FIG. 4, the adjustment valve 26 fully opens and the cuff pressure is released. Then, as shown in step S8, the CPU 10 functions as the display processing unit to display the measurement result on the display screen 40 (see FIG. 2) provided on the upper surface of the main unit 101. Also, the CPU 10 stores the measurement result of the current instance and the accumulated total number of instances of measurement (indicated by the reference sign N) in the storage apparatus 8 shown in FIG. 3.

Mode Setting and Measurement Capability Diagnosis Processing

Figure 8:
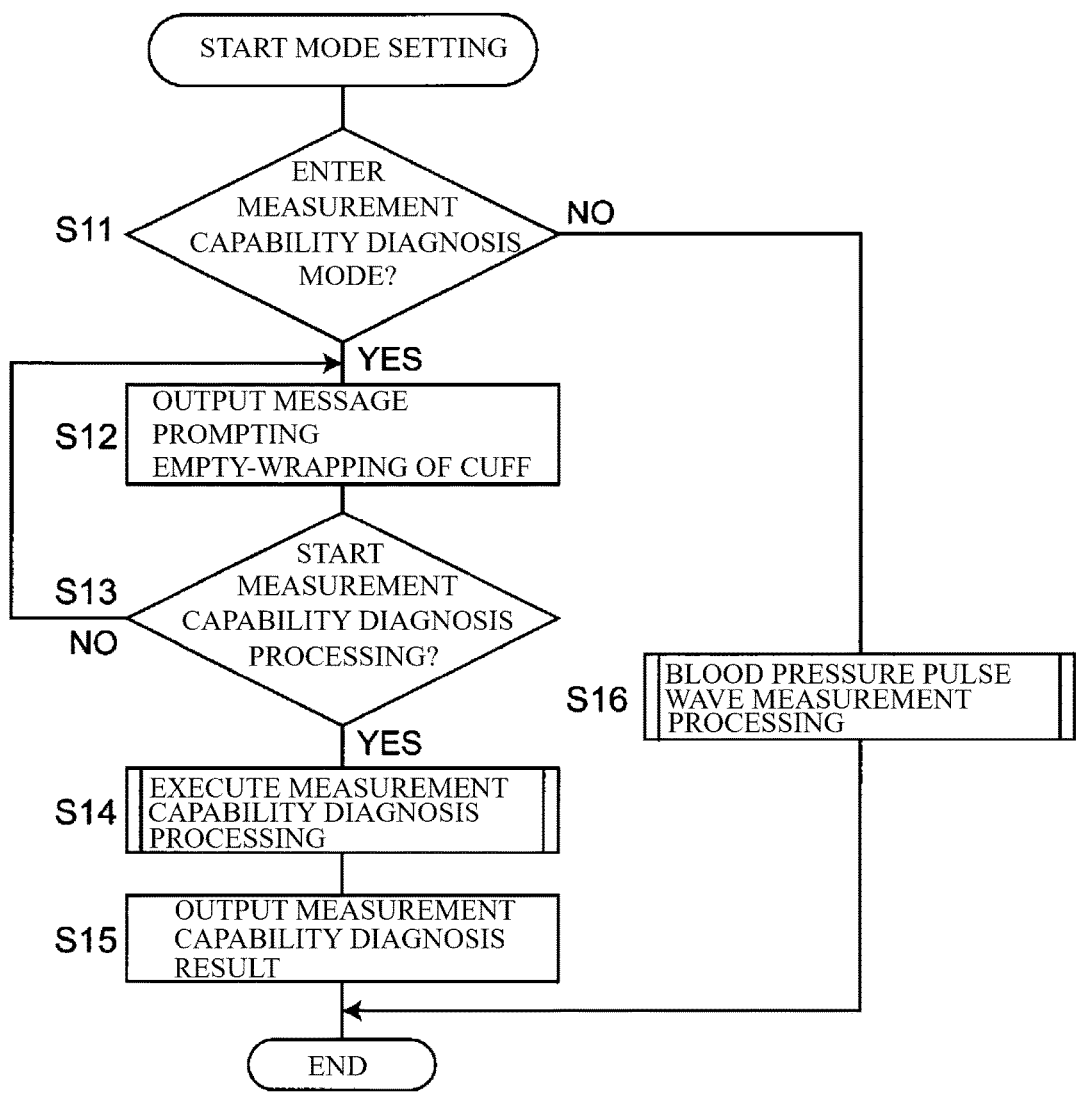
FIG. 8 is a diagram showing flows for mode setting and measurement capability diagnosis processing performed by the blood pressure pulse wave measurement apparatus.

FIG. 8 shows a flow of mode setting and measurement capability diagnosis processing performed by the control unit 2 (in particular, the CPU 10) of the blood pressure pulse wave measurement apparatus 100.

When the user inputs a mode setting instruction using the operation unit 6, as shown in step S11 of FIG. 8, the control unit 2 performs display asking the user whether or not to enter a measurement capability diagnosis mode, such as "Perform measurement capability diagnosis?", on the display screen 40 of the main unit 101. Here, if the user has selected not to enter the measurement capability diagnosis mode (NO in step S11 of FIG. 8), the processing advances to step S16, and the control unit 2 enters a mode of performing blood pressure measurement, for example, and executes the above-mentioned blood pressure pulse wave measurement processing (the flow shown in FIG. 4).

On the other hand, if the user inputs the instruction "enter measurement capability diagnosis mode" using the operation unit 6 (YES in step S11 of FIG. 8), as shown in step S12 of FIG. 8, the control unit 2 outputs a message prompting empty-wrapping of the cuff 24 to the display screen 40 of the main unit 101. For example, as illustrated in FIG. 15, the message "Please empty-wrap all of the cuffs to the smallest calibration mark positions in the circumferential length, then press the measure button." is displayed. Here, "empty-wrapping" means wrapping only the cuff 24 into a cylinder shape with nothing in the center instead of wrapping the cuff 24 around the measurement site.

Figure 10A:
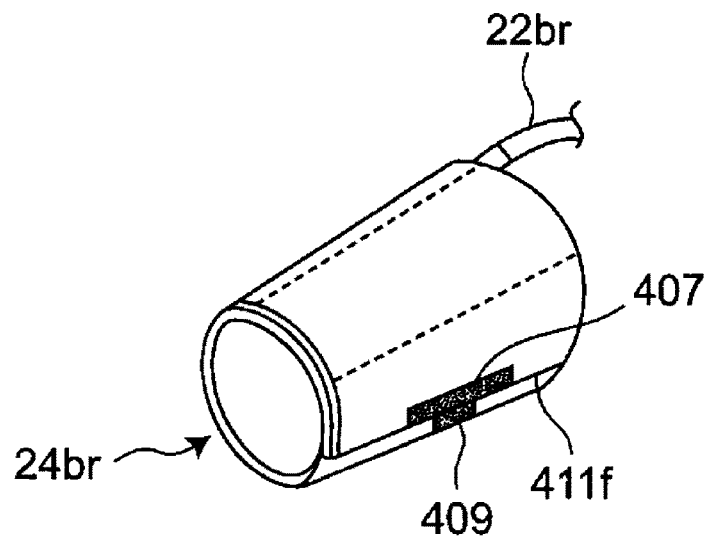
FIG. 10A is a perspective view showing a state in which the cuff of the blood pressure pulse wave measurement apparatus is empty-wrapped into a cylindrical shape.
Figure 10B:
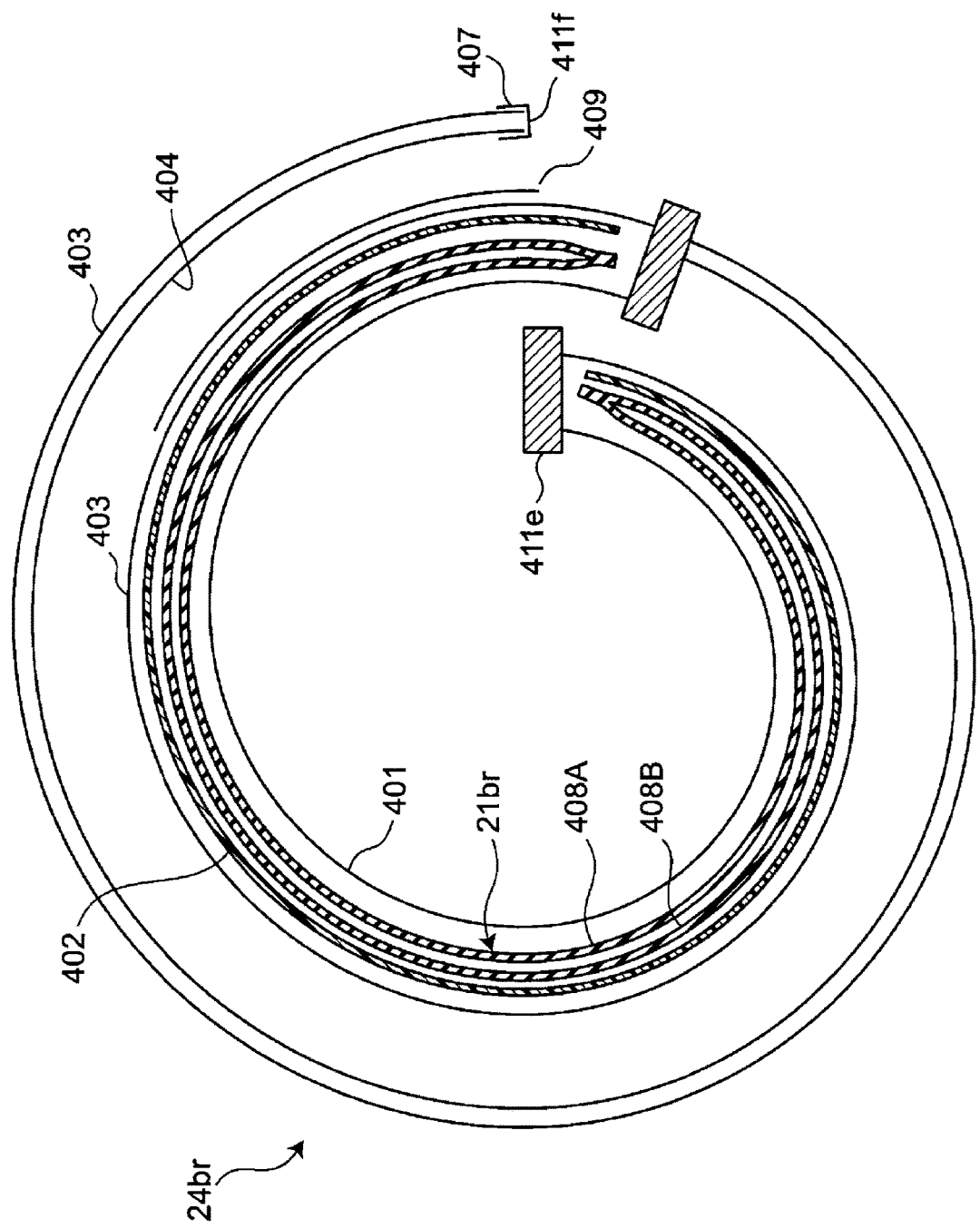
FIG. 10B is a cross-sectional view showing a state in which the cuff of the blood pressure pulse wave measurement apparatus is empty-wrapped into a cylindrical shape.

Upon seeing this message, the user empty-wraps all of the cuffs 24 (cuff 24br is shown in this example) as shown in FIG. 10A (perspective view) and FIG. 10B (cross-sectional view), for example, and aligns the positioning mark 407 on the outer circumferential end 411f with the position of the calibration mark 409 at which the circumferential length (dimension around the cylinder of the cuff 24) is the smallest. At this time, because of the calibration marks 409, the circumferential lengths of the cuffs are constant, and according to this circumferential length, the volumes of the fluid bladders 21 in the cuffs 24 are restricted to a certain amount with good reproducibility. Also, since the curler 402 is the core (the curler 402 is bent such that the curvature increases from the natural state, generating a repulsive force), the cuff 24 is strongly empty-wrapped with ease into a cylinder shape. As a result, the accuracy of determining whether or not there is a later-described failure increases.

Next, when the user inputs an instruction to start measurement capability diagnosis using the operation unit 6 (YES in step S13 of FIG. 8), the processing advances to step S14 of FIG. 8, and the control unit 2 functions as a self failure diagnosis unit and executes measurement capability diagnosis processing.

Figure 11:
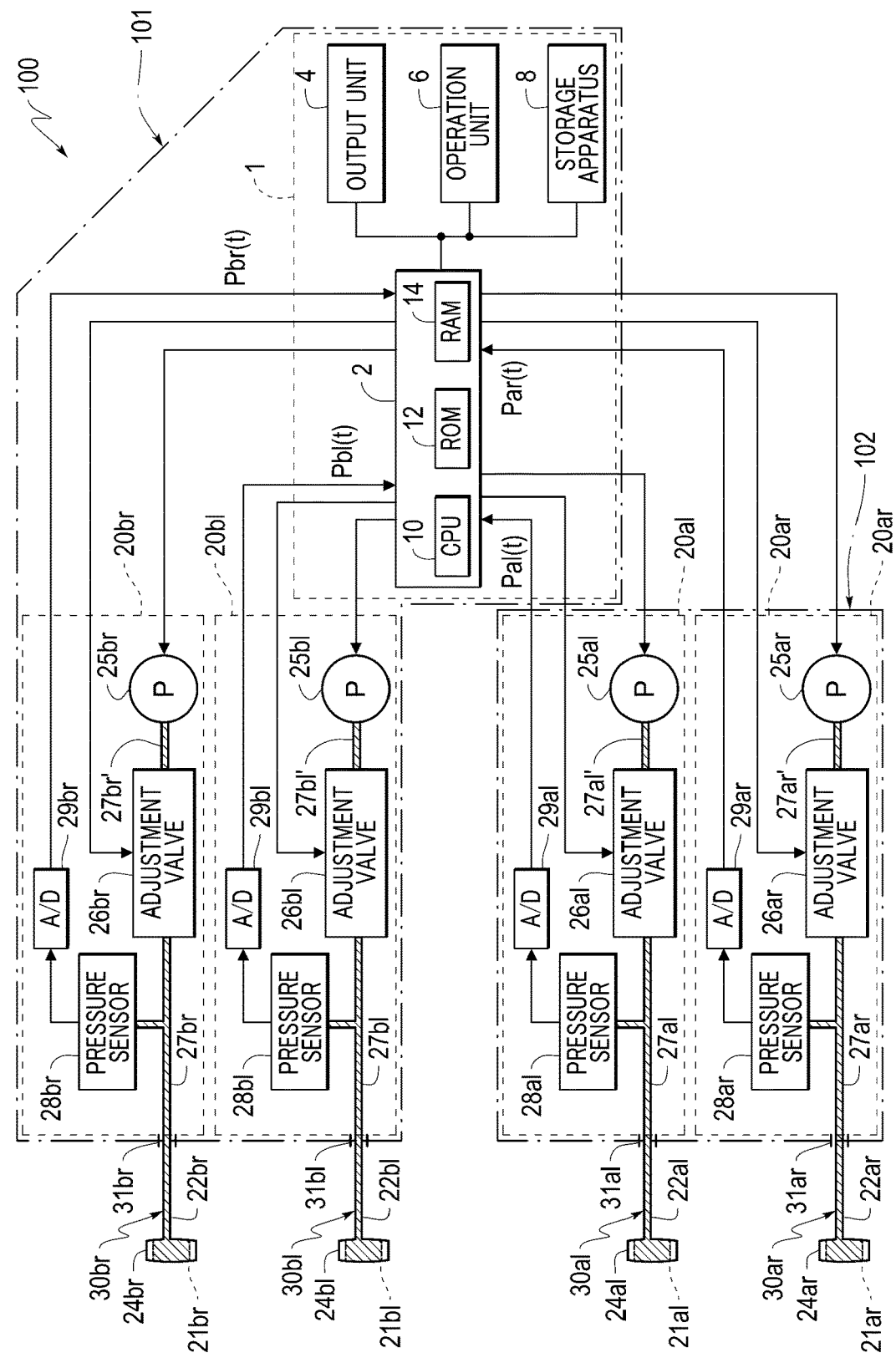
FIG. 11 is a diagram showing a fluid system to be subjected to measurement capability diagnosis by the blood pressure pulse wave measurement apparatus.

Here, in FIG. 11, the fluid systems 30ar, 30al, 30br, and 30bl corresponding to the cuffs 24ar, 24al, 24br, and 24bl, which are to be subjected to the measurement capability diagnosis, are indicated with diagonal lines. The fluid system 30ar corresponding to the cuff 24ar includes a pressure pump 25ar, an adjustment valve 26ar, a pressure sensor 28ar, inner pumps 27ar and 27ar', a connecting pipe 22ar, and a fluid bladder 21ar. The fluid system 30al corresponding to the cuff 24al includes a pressure pump 25al, an adjustment valve 26al, a pressure sensor 28al, inner pipes 27al and 27al', a connecting pipe 22al, and a fluid bladder 21al. The fluid system 30br corresponding to the cuff 24br includes a pressure pump 25br, an adjustment valve 26br, a pressure sensor 28br, inner pipes 27br and 27br', a connecting pipe 22br, and a fluid bladder 21br. The fluid bladder 30bl corresponding to the cuff 24bl includes a pressure pump 25bl, an adjustment valve 26bl, a pressure sensor 28bl, inner pipes 27bl and 27bl', a connecting pipe 22bl, and a fluid bladder 21bl. In this example, the capacities of the fluid systems 30ar, 30al, 30br, and 30bl are each about 300 cc and include the restricted capacities of the fluid bladders 21ar, 21al, 21br, and 21bl in the corresponding cuffs.

In this example, the control unit 2 executes the measurement capability diagnosis processing in parallel with the same flow on the fluid systems 30ar, 30al, 30br, and 30bl. Accordingly, the control unit 2 determines whether or not a failure has occurred in the fluid systems 30ar, 30al, 30br, and 30bl corresponding to any of the multiple cuffs 24ar, 24al, 24br, and 24bl.

In the following description, the fluid systems 30ar, 30al, 30br, and 30bl will be collectively referred to as "fluid systems 30" if there is no need to make a distinction therebetween.

Figure 9:
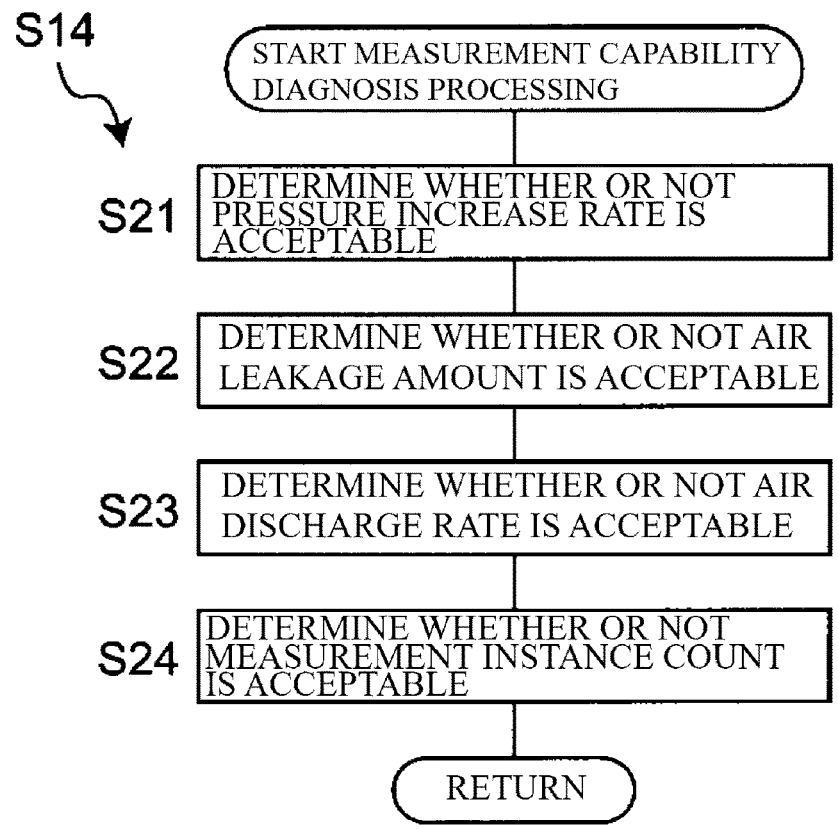
FIG. 9 is a diagram showing details of a flow for measurement capability diagnosis processing performed by the blood pressure pulse wave measurement apparatus on fluid systems.

FIG. 9 shows details of the flow of measurement capability diagnosis processing (step S14 of FIG. 8) performed by the control unit 2 on the fluid systems 30.

Figure 12:
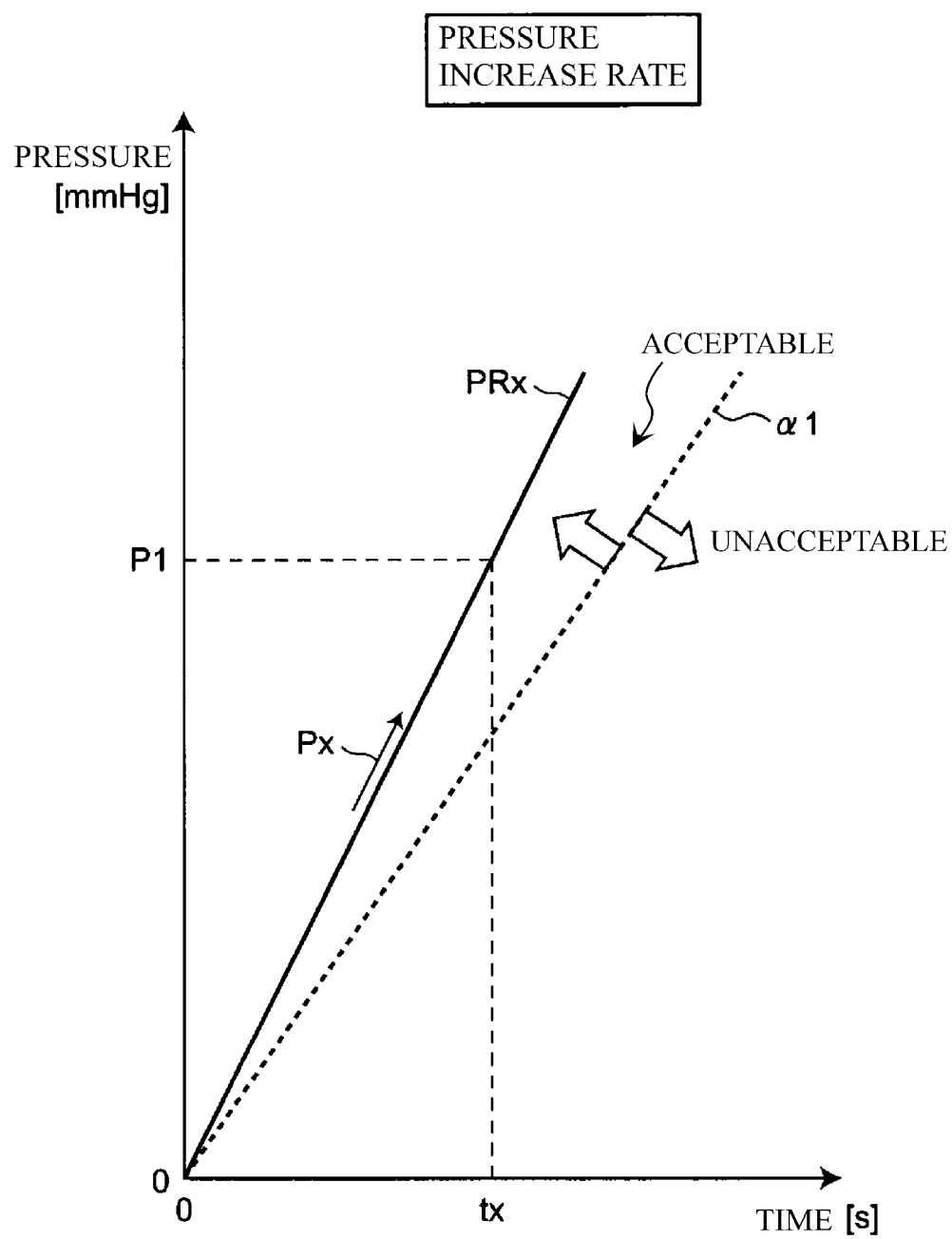
FIG. 12 is a diagram schematically illustrating a method for determining whether or not a pressure increase rate is acceptable.

First, in step S21 of FIG. 9, the control unit 2 determines whether or not the pressure increase rate is acceptable. Specifically, as shown in FIG. 12, in a state in which the adjustment valve 26 is closed to the atmosphere, the pressure pump 25 is caused to operate at a constant driving voltage, and the pressure Px of the fluid system 30 is increased from 0 mmHg to a reference pressure P1 (in this example, P1=285 mmHg). Then, the time tx that it takes for the pressure Px of the fluid system 30 to reach the reference pressure P1 is measured, and the pressure increase rate PRx (=P1/tx) at this time is calculated. If the calculated pressure increase rate PRx is a lower limit value $\alpha 1$ or more, it is determined as being "acceptable". On the other hand, if the calculated pressure increase rate Pvx is less than the lower limit value $\alpha 1$, it is determined as being "unacceptable". In this example, according to the restricted capacity (about 300 cc) of the fluid system 30, the lower limit value for the pressure increase rate PRx is set in advance to $\alpha 1 = 4.8$ mmHg/s. Accordingly, it is possible to suitably determine whether or not the pressure increase rate is acceptable.

Figure 13:
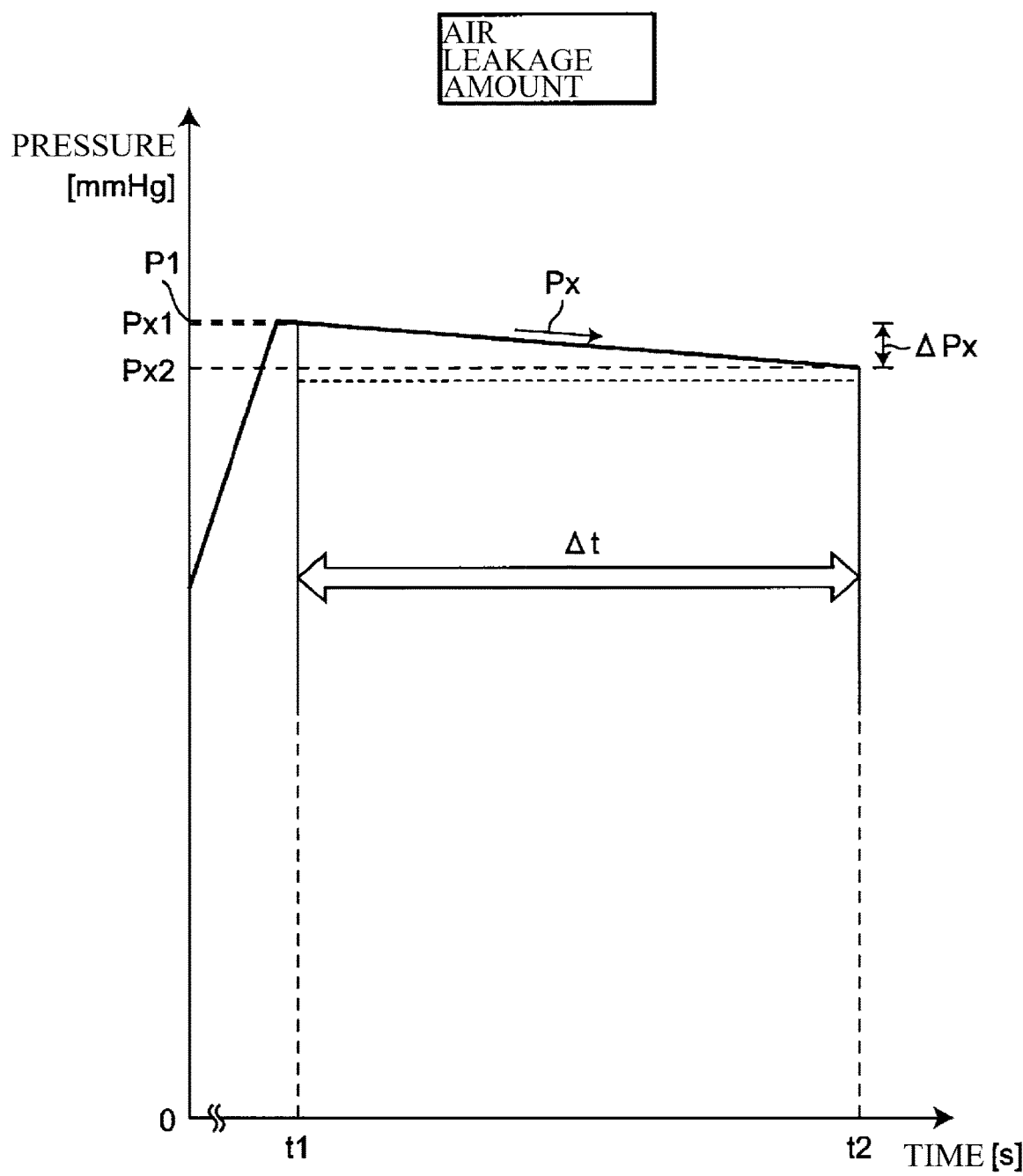
FIG. 13 is a diagram schematically illustrating a method for determining whether or not an air leakage amount is acceptable.

Next, in step S22 of FIG. 9, the control unit 2 determines whether or not the air leakage amount is acceptable. Specifically, as shown in FIG. 13, after reaching the reference pressure P1 in order to determine the pressure increase rate, the fluid system 30 is kept in a state of being closed for a certain time period $\Delta t$ (=t2−t1) from a time t1 to a time t2. In this example, $\Delta t$ is set to 60 s (seconds). Then, the pressure Px1 of the fluid system 30 at the time t1 and the pressure Px2 of the fluid system 30 at the time t2 are measured and the pressure difference $\Delta Px$ (=Px1−Px2) is calculated. If the calculated pressure difference $\Delta Px$ is an upper limit value $\alpha 2$ or less, it is determined as being "acceptable". On the other hand, if the calculated pressure difference $\Delta Px$ exceeds the upper limit value $\alpha 2$, it is determined as being "unacceptable". In this example, according to the restricted capacity (about 300 cc) of the fluid system 30, the upper limit value for the air leakage amount is set in advance to α2=6.0 mmHg/60 s. Accordingly, it is possible to suitably determine whether or not the air leakage amount is acceptable.

Figure 14:
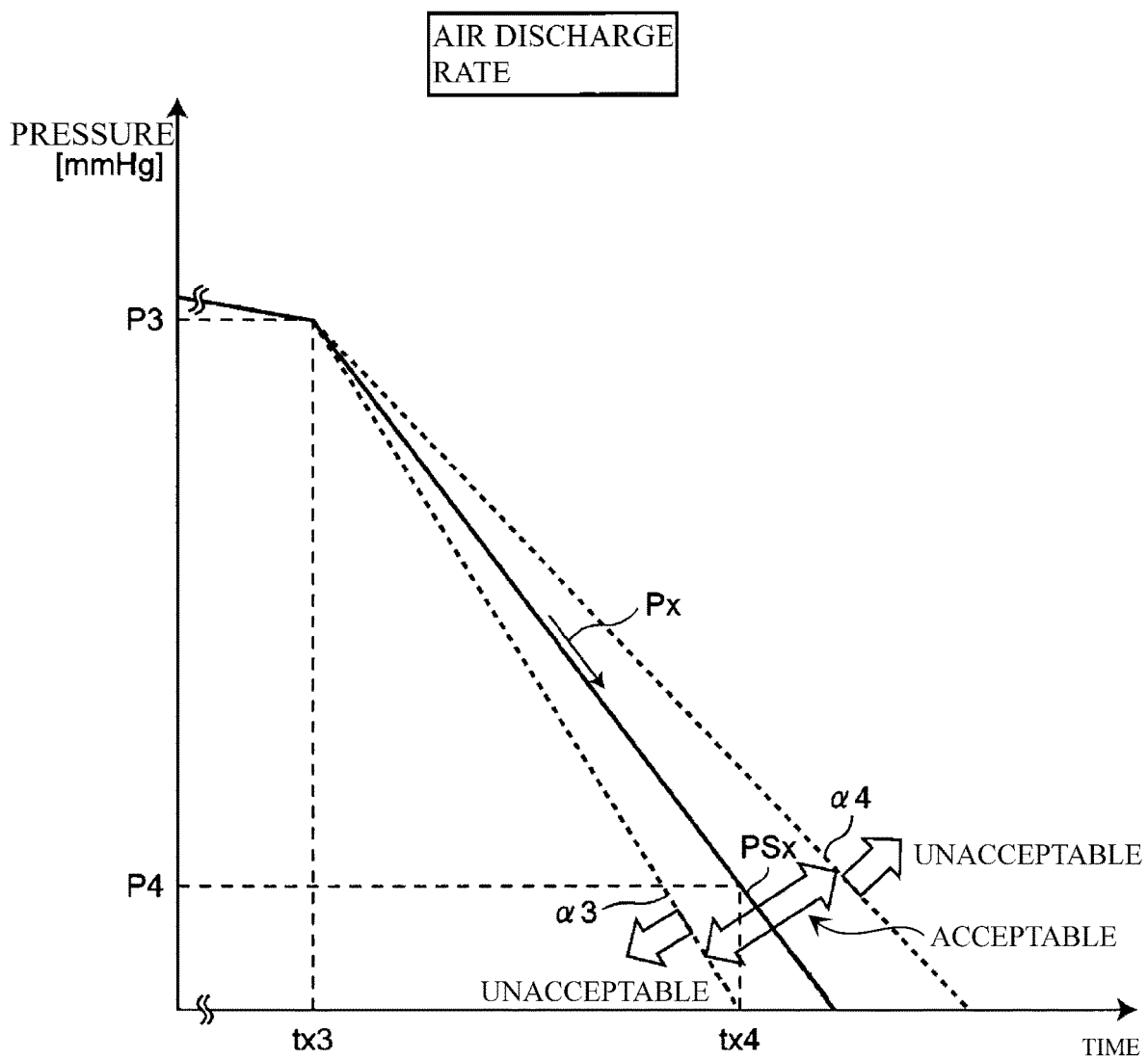
FIG. 14 is a diagram schematically illustrating a method for determining whether or not an air discharge rate is acceptable.

Next, in step S23 of FIG. 9, the control unit 2 determines whether or not the air discharge rate is acceptable. Specifically, after the adjustment valve 26 is opened and the air in the fluid system 30 is discharged, in a state in which the adjustment valve 26 is closed to the atmosphere, the pressure pump 25 is caused to operate at a certain drive voltage, and the pressure Px of the fluid system 30 is increased to a pressure exceeding the reference pressure P3 (in this example, P3=285 mmHg). Thereafter, as shown in FIG. 14, the adjustment valve 26 is opened with a certain opening degree to the atmosphere at the time tx3, and the pressure Px of the fluid system 30 is reduced from the reference pressure P3 to a lower reference pressure P4 (in this example, P4=40 mmHg). Then, the time tx4 at which the pressure Px of the fluid system 30 reaches the reference pressure P4 is measured, and the air discharge rate PSx (=(P3−P2)/(tx4−tx3)) is calculated. If the calculated air discharge rate PSx is a lower limit value α3 or more and an upper limit value α4 or less, it is determined as being "acceptable". On the other hand, if the calculated air discharge rate PSx is less than the lower limit value α3 or exceeds the upper limit value α4, it is determined as being "unacceptable". In this example, according to the restricted capacity (about 300 cc) of the fluid system 30, the lower limit value for the air discharge rate PSx is set in advance to α3=3.5 mmHg/s and the upper limit value is set in advance to α4=6.0 mmHg/s. Accordingly, it is possible to suitably determine whether or not the air discharge rate is acceptable.

Next, in step S24 of FIG. 9, the control unit 2 determines whether or not the accumulated total measurement instance count has exceeded an upper limit instance count. Specifically, the control unit 2 reads out the accumulated total measurement instance count N stored in the storage apparatus 8 shown in FIG. 3 and compares it with a predetermined upper limit instance count UL. Then, if the accumulated total measurement instance count N is less than or equal to the upper limit instance count UL, it is determined as being "acceptable". On the other hand, if the accumulated total measurement instance count N exceeds the upper limit instance count UL, it is determined as being "unacceptable". In this example, the upper limit instance count UL is set in advance to 60000.

The amount of time needed for the processing from step S21 to step S24 in FIG. 9 is about 4 minutes in total in this example.

For each measurement item, a correlational relationship between the measured numeric value (measurement value) and the determination result is displayed as shown in the following Table 1. Note that the significant figures of the measurement values for the air leakage amount, the pressure increase rate, and the air discharge rate are two digits in this example.

TABLE 1

| Measurement Item | Measurement Value | Measurement Result |
| --- | --- | --- |
| Air leakage amount | 0 to 6.0 mmHg/60 s | ○ |
|  | 6.1 mmHg/60 s or more | x |
| Pressure increase rate | 4.8 mmHg/s or more | ○ |
|  | 4.7 mmHg/s or less | x |
| Air discharge rate | 3.5 mmHg/s to 6.0 mmHg/s | ○ |

TABLE 1-continued

| Measurement Item | Measurement Value | Measurement Result |
| --- | --- | --- |
|  | 3.4 mmHg/s or less, 6.1 mmHg or more | x |
| Measurement instance count | 0 to 60000 | ○ |
|  | 60001 or more | x |

In this manner, the control unit 2 executes the measurement capability diagnosis processing from steps S21 to S24 in FIG. 9 in parallel on the multiple fluid systems 30ar, 30al, 30br, and 30bl. Accordingly, it is possible to determine whether or not a failure has occurred in a fluid system 30 corresponding to any of the multiple cuffs 24, and it is possible to determine whether or not a failure has occurred regarding any of the multiple measurement items. Accordingly, it is possible to determine whether or not there are various kinds of failures in the fluid system 30 due to the user only performing a simple operation (mainly an operation of empty-wrapping the cuff 24) without using a special tool.

When the measurement capability diagnosis for the fluid systems 30 is complete, as shown in step S15 of FIG. 8, the control unit 2 causes the output unit 4 to operate as a first output unit and a second output unit and outputs the result of the measurement capability diagnosis.

FIG. 16 illustrates the result of the measurement capability diagnosis displayed on the display screen 40 of the main unit 101 by the output unit 4. In this example, the title "maintenance menu>measurement capability diagnosis" is displayed in the uppermost line. Below that, the diagnosis results are displayed in a table format. In this table of diagnosis results, the displays "right upper arm", "left upper arm", "right ankle", and "left ankle" at the top of the table correspond to the diagnosed fluid systems 30br, 30bl, 30ar, and 30al. The displays "air leakage amount", "pressure increase rate", "air discharge rate", and "measurement instance count" on the side of the table correspond to the four measurement items. In the table body, "○" and "x" indicate whether or not the respective determination results for the corresponding measurement items of each corresponding fluid system 30 are acceptable (i.e., whether or not there is a failure).

According to the example shown in FIG. 16, the user can find out that the determination result for the air leakage amount is "unacceptable", the determination result for the pressure increase rate is "acceptable", the determination result for the air discharge rate is "acceptable", and the determination result for the measurement instance count is "acceptable" for the fluid system 30br corresponding to the "right upper arm". Also, the user can find out that the determination results for the air leakage amount, the pressure increase rate, the air discharge rate, and the measurement instance count are all "acceptable" for the fluid system 30bl corresponding to the "left upper arm". Similarly, the user can find out that the determination results for the air leakage amount, the pressure increase rate, the air discharge rate, and the measurement instance count are all "acceptable" for the fluid system 30ar corresponding to the "right ankle" and the fluid system 30al corresponding to the "left ankle" as well. In this manner, the user can find out the results of determining whether or not there is a failure for each fluid system 30 corresponding to the cuffs 24 and for each measurement item.

FIG. 17 illustrates the results of the measurement capability diagnosis, which have been printed out by a printer (not shown) serving as the output unit 4. With this printout, the title "measurement capability diagnosis" is displayed on the left end outside of a frame 71 (at the upper portion), and the year, month, day, and time of output (in this example, "2016/02/23 17:25") are displayed on the right end. "Diagnosis results" are displayed in a table format in the upper portion in the frame 71. Below that, "overall results" are displayed as text.

The method of viewing the "Diagnosis Results" table shown in FIG. 17 is set to be the same as the method of viewing the diagnosis results on the display screen 40 shown in FIG. 16. Accordingly, the user can find out the results of determining whether or not there is a failure for each fluid system 30 corresponding to the cuffs 24 and for each measurement item. Furthermore, in the "Diagnosis Results" table, directly below the "○"'s and "×"'s in the table body, numeric values indicating the measured air leakage amount, pressure increase rate, air discharge rate, and measurement instance count are displayed. Accordingly, the user can also find out the bases for the respective determinations.

In the example of the "diagnosis results" shown in FIG. 17, the result of determining the air discharge amount is "unacceptable" for the fluid system 30br corresponding to the "right upper arm". There is no problem with the other measurement items for the fluid system 30br and the other fluid systems 30bl, 30ar, and 30al. In response to this, the message "<Right upper arm> A decrease in measurement capability has been detected. Please re-wrap the cuff, press the measurement button, and carry out diagnosis again. If the same result is displayed again, please receive maintenance service." is displayed in the "overall results" field in FIG. 17. The message "There is no problem with the measurement capability." is displayed for each of the other fluid systems 30bl, 30ar, and 30al corresponding to the "left upper arm", "right ankle", and "left ankle". Upon seeing these messages, the user can find out specifically how to deal with the current state of the measurement capability of the apparatus. For example, if the user seeing these messages is a medical professional, he or she can quickly deal with the problem by calling a maintenance serviceman or the like.

The above-described embodiment described an example in which the cuffs 24ar, 24al, 24br, and 24bl are attached only to the right ankle, left ankle, right upper arm, and left upper arm. However, there is no limitation to this. The measurement site to which the cuffs 24ar, 24al, 24br, and 24bl are to be attached may be a wrist, a fingertip, or the like.

Also, the number of cuffs 24 subjected to the measurement capability diagnosis and the number of fluid systems 30 corresponding to the cuffs 24 are not limited to four, and for example, may be only one, only two, or another number.

Also, the invention can also be applied to a so-called integral-type blood pressure monitor in which a cuff and a main body provided with elements for blood pressure measurement are constituted integrally via a short cylindrical connecting pipe.

The above-described embodiments are exemplary, and various modifications are possible without departing from the scope of the invention. The above-described multiple embodiments can be achieved independently, and the embodiments can also be combined. Also, the various features of the different embodiments can also be achieved independently, and the features of the different embodiments can also be combined.

REFERENCE SIGNS LIST

2 Control unit
21, 21ar, 21al, 21br, 21bl Fluid bladder
22, 22ar, 22al, 22br, 22bl Connecting pipe
24, 24ar, 24al, 24br, 24bl Cuff
25, 25ar, 25al, 25br, 25bl Pressure pump
26, 26ar, 26al, 26br, 26bl Adjustment valve
27, 27ar, 27al, 27br, 27bl, 27', 27ar', 27al', 27br', 27bl' Inner pipe
30, 30br, 30bl, 30ar, 30al Fluid system
40 Display screen
100 Blood pressure pulse wave measurement apparatus
401 Inner cloth
402 Curler
403 Outer cloth
409 Calibration mark

The invention claimed is:

1. A blood pressure monitor for performing blood pressure measurement, comprising:
   a cuff to be wrapped around a measurement site;
   a unit including, as elements for blood pressure measurement, a pump, a valve, a pressure sensor, and an inner pipe connecting the pump, valve, and pressure sensor such that fluid can pass therethrough; and
   a connecting pipe connecting the cuff and the inner pipe in the unit such that fluid can pass therethrough,
   wherein the cuff is provided with marks serving as references for setting a dimension around a cylinder of the cuff when empty-wrapping, in which only the cuff is wrapped into a cylindrical shape with nothing in the center of the cuff, is performed, and
   the blood pressure monitor further comprising:
   an operation unit operated by a user for selecting a mode between a blood pressure measurement mode and a measurement capability diagnosis mode; and
   a processor configured to operate in either one of the blood pressure measurement mode and the measurement capability diagnosis mode selectable by the operation unit, in which,
      under the blood pressure measurement mode, the cuff is wrapped around the measurement site and a blood pressure measurement is conducted using the unit and the connecting pipe, and
      under the measurement capability diagnosis mode, the cuff is held in the cylindrical shape to form an empty-wrapped state with no measurement site in the cylindrical shape and a self failure diagnosis test is conducted using the unit and the connecting pipe such that the self failure diagnosis test includes at least measurement items of a pressure increase rate, an air leakage amount, and an air discharge rate which are conducted sequentially so as to find a failure in a fluid system including the pump, the valve, the pressure sensor, the inner pipe, the connecting pipe, and the cuff.

2. The blood pressure monitor according to claim 1, wherein
   lower limit values and upper limit values are set in advance for the measurement items and
   the processor determines whether or not the plurality of measurement items including at least the pressure increase rate, the air leakage amount, and the air discharge rate are acceptable by comparing the plurality of measurement items with the upper limit values or the lower limit values set in advance according to the restricted capacity of the fluid system.

3. The blood pressure monitor according to claim 1, wherein
   the cuff contains a fluid bladder that is in communication with the connecting pipe between an inner cloth that is to come into contact with the measurement site and an outer cloth opposing the inner cloth, and a curler that keeps the shape of the cuff in a cylindrical shape to be wrapped around the measurement site in a natural state and is a core in the empty-wrapped state is included between the outer cloth and the fluid bladder.

4. The blood pressure monitor according to claim 1, wherein
the cuff is provided with calibration marks in a lengthwise direction of the cuff as the marks.

5. The blood pressure monitor according to claim 2, comprising
a first output unit configured to output results of determining whether or not each of the plurality of measurement results is acceptable.

6. The blood pressure monitor according to claim 1, wherein
a plurality of the cuffs are provided,
the unit includes an element for blood pressure measurement, corresponding to each cuff,
the cuffs and the corresponding inner pipes in the unit are connected by the connecting pipe, and
the processor determines whether or not there is a failure in each fluid system corresponding to the cuffs.

7. The blood pressure monitor according to claim 6, comprising
a second output unit configured to output results of determining whether or not there is a failure in each fluid system corresponding to the cuffs.

* * * * *